(12) United States Patent
Johnson

(10) Patent No.: US 7,763,342 B2
(45) Date of Patent: Jul. 27, 2010

(54) TEAR-RESISTANT THIN FILM METHODS OF FABRICATION

(75) Inventor: A. David Johnson, San Leandro, CA (US)

(73) Assignee: TiNi Alloy Company, San Leandro, CA (US)

( * ) Notice: Subject to any disclaimer, the term of this patent is extended or adjusted under 35 U.S.C. 154(b) by 859 days.

(21) Appl. No.: 11/396,234

(22) Filed: Mar. 31, 2006

(65) Prior Publication Data
US 2006/0232374 A1 Oct. 19, 2006

Related U.S. Application Data

(60) Provisional application No. 60/666,325, filed on Mar. 31, 2005.

(51) Int. Cl.
*B32B 3/26* (2006.01)
(52) U.S. Cl. ..................................... 428/156
(58) Field of Classification Search ................... 428/156
See application file for complete search history.

(56) References Cited

U.S. PATENT DOCUMENTS

| | | |
|---|---|---|
| 368,425 A | 8/1887 | Ross et al. |
| 538,593 A | 4/1895 | Naylor, Jr. |
| 1,560,335 A | 11/1925 | Czochralski |
| 1,904,828 A | 4/1933 | Green |
| 1,926,925 A | 9/1933 | Wescott |
| 2,060,593 A | 11/1936 | Schaurte et al. |
| 2,371,614 A | 3/1945 | Graves |
| 2,586,556 A | 2/1952 | Mullikin |
| 2,608,996 A | 9/1952 | Forman |
| 2,610,300 A | 9/1952 | Walton et al. |
| 2,647,017 A | 7/1953 | Coulliette |
| 2,911,504 A | 11/1959 | Cohn |
| 3,229,956 A | 1/1966 | White |
| 3,351,463 A | 11/1967 | Rozner et al. |
| 3,357,432 A | 12/1967 | Sparks |
| 3,400,906 A | 9/1968 | Stocklin |
| 3,408,890 A | 11/1968 | Bochman, Jr. |

(Continued)

FOREIGN PATENT DOCUMENTS

EP 0053596 6/1982

(Continued)

OTHER PUBLICATIONS

Johnson, David et al.; U.S. Appl. No. 12/019,553 entitled "Frangible shape memory alloy fire sprinkler valve actuator," filed Jan. 24, 2008.

(Continued)

*Primary Examiner*—William P Watkins, III
(74) *Attorney, Agent, or Firm*—Shay Glenn LLP

(57) ABSTRACT

A thin film device and fabrication method providing optimum tear resistance. A thin film layer is formed with a first and second of rows of holes. The holes in each row are spaced-apart along an axis which extends along an edge of the layer. The holes in one row are in overlapping relationship with adjacent holes in the other row. The holes have a diameter which is sufficiently large so that an imaginary line extending perpendicular from any location along the edge will intersect at least one hole, thus preventing further propagation of any tears or cracks which start from the edge.

15 Claims, 2 Drawing Sheets

U.S. PATENT DOCUMENTS

| | | | |
|---|---|---|---|
| 3,435,823 A | 4/1969 | Edwards |
| 3,445,086 A | 5/1969 | Quinn |
| 3,454,286 A | 7/1969 | Anderson et al. |
| 3,546,996 A | 12/1970 | Grijalva et al. |
| 3,561,537 A | 2/1971 | Dix et al. |
| 3,613,732 A | 10/1971 | Willson et al. |
| 3,620,212 A | 11/1971 | Fannon, Jr. et al. |
| 3,659,625 A | 5/1972 | Coiner et al. |
| 3,725,835 A | 4/1973 | Hopkins et al. |
| 3,789,838 A | 2/1974 | Fournier et al. |
| 3,849,756 A | 11/1974 | Hickling |
| 3,888,975 A | 6/1975 | Ramwell |
| 3,918,443 A | 11/1975 | Vennard et al. |
| 3,974,844 A | 8/1976 | Pimentel |
| 4,055,955 A | 11/1977 | Johnson |
| 4,063,831 A | 12/1977 | Meuret |
| 4,072,159 A | 2/1978 | Kurosawa |
| 4,096,993 A | 6/1978 | Behr |
| 4,151,064 A | 4/1979 | Kuehnle |
| 4,176,719 A | 12/1979 | Bray |
| 4,177,327 A | 12/1979 | Mathews |
| 4,196,045 A | 4/1980 | Ogden |
| 4,243,963 A | 1/1981 | Jameel et al. |
| 4,265,684 A | 5/1981 | Boll |
| 4,279,790 A | 7/1981 | Nakajima |
| 4,340,049 A | 7/1982 | Munsch |
| 4,485,545 A | 12/1984 | Caverly |
| 4,501,058 A | 2/1985 | Schutzler |
| 4,524,343 A | 6/1985 | Morgan et al. |
| 4,549,717 A | 10/1985 | Dewaegheneire |
| 4,551,974 A | 11/1985 | Yaeger et al. |
| 4,553,393 A | 11/1985 | Ruoff |
| 4,558,715 A | 12/1985 | Walton et al. |
| 4,567,549 A | 1/1986 | Lemme |
| 4,585,209 A | 4/1986 | Aine et al. |
| 4,589,179 A | 5/1986 | Hulting, Jr. |
| 4,596,483 A | 6/1986 | Gabriel et al. |
| 4,619,284 A | 10/1986 | Delarue et al. |
| 4,654,191 A | 3/1987 | Krieg |
| 4,684,913 A | 8/1987 | Yaeger |
| 4,706,758 A | 11/1987 | Johnson |
| 4,753,465 A | 6/1988 | Dalby |
| 4,821,997 A | 4/1989 | Zdeblick |
| 4,823,607 A | 4/1989 | Howe et al. |
| 4,824,073 A | 4/1989 | Zdeblick |
| 4,848,388 A | 7/1989 | Waldbusser |
| 4,854,797 A | 8/1989 | Gourd |
| 4,864,824 A | 9/1989 | Gabriel et al. |
| 4,893,655 A | 1/1990 | Anderson |
| 4,896,728 A | 1/1990 | Wolff et al. |
| 4,943,032 A | 7/1990 | Zdeblick |
| 5,060,888 A | 10/1991 | Vezain et al. |
| 5,061,137 A | 10/1991 | Gourd |
| 5,061,914 A | 10/1991 | Busch et al. |
| 5,069,419 A | 12/1991 | Jerman |
| 5,072,288 A | 12/1991 | MacDonald et al. |
| 5,114,504 A | 5/1992 | AbuJudom, II et al. |
| 5,116,252 A | 5/1992 | Hartman |
| 5,117,916 A | 6/1992 | Ohta et al. |
| 5,119,555 A | 6/1992 | Johnson |
| 5,129,753 A | 7/1992 | Wesley et al. |
| 5,160,233 A | 11/1992 | McKinnis |
| 5,190,546 A | 3/1993 | Jervis |
| 5,192,147 A | 3/1993 | McCloskey |
| 5,211,371 A | 5/1993 | Coffee |
| 5,218,998 A | 6/1993 | Bakken et al. |
| 5,245,738 A | 9/1993 | Johnson |
| 5,309,717 A | 5/1994 | Minch |
| 5,312,152 A | 5/1994 | Woebkenberg, Jr. et al. |
| 5,325,880 A | 7/1994 | Johnson et al. |
| 5,344,117 A | 9/1994 | Trah et al. |
| 5,364,046 A | 11/1994 | Dobbs et al. |
| 5,494,113 A | 2/1996 | Polan |
| 5,502,982 A | 4/1996 | Venetucci |
| 5,543,349 A | 8/1996 | Kurtz et al. |
| 5,605,543 A | 2/1997 | Swanson |
| 5,619,177 A | 4/1997 | Johnson et al. |
| 5,622,225 A | 4/1997 | Sundholm |
| 5,640,217 A | 6/1997 | Hautcoeur et al. |
| 5,641,364 A | 6/1997 | Golberg et al. |
| 5,676,356 A | 10/1997 | Ekonen et al. |
| 5,695,504 A | 12/1997 | Gifford, III et al. |
| 5,714,690 A | 2/1998 | Burns et al. |
| 5,722,989 A | 3/1998 | Fitch et al. |
| 5,771,742 A | 6/1998 | Bokaie et al. |
| 5,772,378 A | 6/1998 | Keto-Tokoi |
| 5,796,152 A | 8/1998 | Carr et al. |
| 5,819,749 A | 10/1998 | Lee et al. |
| 5,825,275 A | 10/1998 | Wuttig et al. |
| 5,837,394 A | 11/1998 | Schumm, Jr. |
| 5,840,199 A | 11/1998 | Warren |
| 5,850,837 A | 12/1998 | Shiroyama et al. |
| 5,867,302 A | 2/1999 | Fleming |
| 5,903,099 A | 5/1999 | Johnson et al. |
| 5,924,492 A | 7/1999 | Kikuchi et al. |
| 5,930,651 A | 7/1999 | Terasawa |
| 5,960,812 A | 10/1999 | Johnson |
| 6,042,553 A | 3/2000 | Solar et al. |
| 6,072,617 A | 6/2000 | Henck |
| 6,073,700 A | 6/2000 | Tsuji et al. |
| 6,075,239 A | 6/2000 | Aksyuk et al. |
| 6,080,160 A | 6/2000 | Chen |
| 6,084,849 A | 7/2000 | Durig et al. |
| 6,101,164 A | 8/2000 | Kado et al. |
| 6,110,204 A | 8/2000 | Lazarov et al. |
| 6,124,523 A * | 9/2000 | Banas et al. ............... 623/1.15 |
| 6,126,371 A | 10/2000 | McCloskey |
| 6,139,143 A | 10/2000 | Brune et al. |
| 6,195,478 B1 | 2/2001 | Fouquet |
| 6,203,715 B1 | 3/2001 | Kim et al. |
| 6,229,640 B1 | 5/2001 | Zhang |
| 6,247,493 B1 | 6/2001 | Henderson |
| 6,277,133 B1 | 8/2001 | Kanesaka |
| 6,284,067 B1 | 9/2001 | Schwartz et al. |
| 6,358,380 B1 | 3/2002 | Mann et al. |
| 6,386,507 B2 | 5/2002 | Dhuler et al. |
| 6,406,605 B1 | 6/2002 | Moles |
| 6,407,478 B1 | 6/2002 | Wood et al. |
| 6,410,360 B1 | 6/2002 | Steenberge |
| 6,447,478 B1 | 9/2002 | Maynard |
| 6,451,668 B1 | 9/2002 | Neumeier et al. |
| 6,454,913 B1 | 9/2002 | Rasmussen et al. |
| 6,470,108 B1 | 10/2002 | Johnson |
| 6,475,261 B1 | 11/2002 | Matsumoto et al. |
| 6,524,322 B1 | 2/2003 | Berreklouw |
| 6,533,905 B2 | 3/2003 | Johnson et al. |
| 6,537,310 B1 | 3/2003 | Palmaz et al. |
| 6,582,985 B2 | 6/2003 | Cabuz et al. |
| 6,592,724 B1 | 7/2003 | Rasmussen et al. |
| 6,605,111 B2 | 8/2003 | Bose et al. |
| 6,614,570 B2 | 9/2003 | Johnson et al. |
| 6,620,634 B2 | 9/2003 | Johnson et al. |
| 6,624,730 B2 | 9/2003 | Johnson et al. |
| 6,669,794 B1 | 12/2003 | Bellouard et al. |
| 6,669,795 B2 | 12/2003 | Johnson et al. |
| 6,672,502 B1 | 1/2004 | Paul et al. |
| 6,688,828 B1 | 2/2004 | Post |
| 6,729,599 B2 | 5/2004 | Johnson |
| 6,742,761 B2 | 6/2004 | Johnson et al. |
| 6,746,890 B2 | 6/2004 | Gupta et al. |
| 6,771,445 B1 | 8/2004 | Hamann et al. |
| 6,790,298 B2 | 9/2004 | Johnson et al. |
| 6,811,910 B2 | 11/2004 | Tsai et al. |
| 6,840,329 B2 | 1/2005 | Kikuchi et al. |

| | | | |
|---|---|---|---|
| 6,843,465 | B1 | 1/2005 | Scott |
| 6,908,275 | B2 | 6/2005 | Nelson et al. |
| 6,920,966 | B2 | 7/2005 | Buchele et al. |
| 6,955,187 | B1 | 10/2005 | Johnson |
| 7,040,323 | B1 | 5/2006 | Menchaca et al. |
| 7,044,596 | B2 | 5/2006 | Park |
| 7,084,726 | B2 | 8/2006 | Gupta et al. |
| 7,201,367 | B2 | 4/2007 | Wietharn |
| 2001/0023010 | A1 | 9/2001 | Yamada et al. |
| 2002/0018325 | A1 | 2/2002 | Nakatani et al. |
| 2002/0062154 | A1 | 5/2002 | Ayers |
| 2002/0106614 | A1 | 8/2002 | Prince et al. |
| 2003/0002994 | A1 | 1/2003 | Johnson et al. |
| 2003/0078465 | A1 | 4/2003 | Pai et al. |
| 2003/0170130 | A1 | 9/2003 | Johnson |
| 2004/0083006 | A1 | 4/2004 | Ellingsen |
| 2004/0200551 | A1 | 10/2004 | Brhel et al. |
| 2004/0243219 | A1 | 12/2004 | Fischer et al. |
| 2004/0249399 | A1 | 12/2004 | Cinquin et al. |
| 2005/0113933 | A1* | 5/2005 | Carter et al. ............... 623/23.7 |
| 2006/0118210 | A1 | 6/2006 | Johnson |
| 2006/0213522 | A1 | 9/2006 | Menchaca et al. |
| 2007/0137740 | A1 | 6/2007 | Johnson et al. |
| 2007/0207321 | A1 | 9/2007 | Abe et al. |
| 2007/0246233 | A1 | 10/2007 | Johnson |
| 2009/0183986 | A1 | 7/2009 | Johnson et al. |

FOREIGN PATENT DOCUMENTS

| | | |
|---|---|---|
| EP | 0310439 | 4/1989 |
| EP | 1122526 | 8/2001 |
| EP | 1238600 | 9/2002 |
| GB | 2187951 | 9/1987 |
| JP | 57161031 | 10/1982 |
| JP | 59179771 | 10/1984 |
| JP | 07090624 | 4/1995 |
| JP | 10173306 | 6/1998 |
| JP | 2000185999 A | 7/2000 |
| SU | 1434314 | 10/1988 |
| WO | WO98/53362 | 11/1998 |
| WO | WO99/62432 | 12/1999 |
| WO | WO00/04204 | 1/2000 |
| WO | WO03/052150 | 6/2003 |
| WO | WO2005/108635 | 11/2005 |
| WO | WO2006/019943 | 2/2006 |

OTHER PUBLICATIONS

Johnson, David et al.; U.S. Appl. No. 10/972,745 entitled "Non-explosive releasable coupling device," filed Oct. 25, 2004.
Xiaogdang, Ma; U.S. Appl. No. 10/972,759 entitled "Magnetic data storage system," filed Oct. 25, 2004.
Johnson, David et al.; U.S. Appl. No. 11/006,501 entitled "Anastomosis device and method," filed Dec. 6, 2004.
Johnson, David et al.; U.S. Appl. No. 11/041,185 entitled "Single crystal shape memory alloy devices and methods," filed Jan. 24, 2005.
Johnson, David; U.S. Appl. No. 11/415,885 entitled "Eyeglass frame," filed May 2, 2006.
Johnson, David; U.S. Appl. No. 11/420,157 entitled "Shape memory allow thin film, method of fabrication, and articles of manufacture," filed May 24, 2006.
Johnson, David; U.S. Appl. No. 11/526,138 entitled "Constant load bolt," filed Sep. 22, 2006.
Johnson, David; U.S. Appl. No. 11/859,697 entitled "Constant load fastener," filed Sep. 21, 2007.
I. E. Viahhi; Robototechnic Constructions Based On CU-AL-NI Single Crystal Actuators; Proceedings of Second International Conference on Shape Memory and Superelastic Technologies; 1997; United States.
Pauling, Linus, College Chemistry, second edition, W.H. Freeman and Company, San Francisco, 1955, pp. 81-91.
Buchaillot L. et al., "Thin film of titanium/nickel shape memory alloy for multi-degree of freedom microactuators", Seisan Kenkyu, vol. 51, No. 8, 1999, pp. 22-23.
Johnson A. D. et al., "Application of shape memory alloys: advantages, disadvantages, and limitations", Micromachining and Microfabrication Process Technology VII, Oct. 22-24, 2001, San Francisco, CA, USA, vol. 4557, 2001, pp. 341-351.
Takabayashi S. et al., "Reversible shape memory alloy film fabricated by RF sputtering", Materials and Manufacturing Processes, vol. 13, No. 2, 1998, pp. 275-286.
Martynov, V., "TiNi thin films for microactuators and microdevices: sputter deposition and processing techniques", Thermec' 2003, Internat'l Conf. on Processing and Manufacturing of Advanced Materials, Jul. 7-11, 2003, Leganes, Madrid, Spain, Materials Science Forum, Jul. 7, 2003 vol. 426-432; pp. 3475-3480.
Johnson, David et al.; U.S. Appl. No. 11/948,852 entitled "Method of alloying reactive elemental components," filed Nov. 30, 2007.
Johnson, David et al.; U.S. Appl. No. 11/949,663 entitled "Hyperelastic shape setting devices and fabrication methods," filed Dec. 3, 2007.
Antonov et al.; New advances and developments in the Stepnakov method for the growth of shaped crystals; Crystallography Reports; vol. 47; Suppl. 1; 2002; pp. S43-S52.
Elastamet™ brochure from New Discovery Metals; 2007.
Elastamet™ website screen capture, accessed Jul. 23, 2008.
Fu et al.; The growth characteristics with a shape memory effect; J. Phys.: Condens. Matter; vol. 4; 1992; pp. 8303-8310.
Morgan; Medical shape memory alloy applications—the market and its products; Materials Science and engineering A 378; 2004; pp. 16-23.
Qingfu et al.; Stabilisation of martensite during training of Cu-Al-Ni single crystals; Journal de Physique IV; Collloqu C2; Supplement to the Journa de Physique III; vol. 5; Feb. 1995; pp. 181-186.
Recarte et al.; Influence of Al and Ni concentration on the martensitic transformation in Cu-Al-Ni shape-memory alloys; Metallurgical and MaterialsTransactions A; vol. 33A; Aug. 2002; pp. 2581-2591.
Sittner et al.; Stress induced martensitic transformations in tension/torsion of CuAlNi single crystal tube; Scripta Materialia; vol. 48; 2003; pp. 1153-1159.
Sutuo et al.; Development of medical guide wire of Cu-Al-Mn-base superelastic alloy with functionally graded characteristics; Mater Res Part B: Appl Biomater; vol. 69B; 2004; pp. 64-69.
Zhang et al.; The variant selection criteria in single-crystal CuAlNi shape memory alloys; Smart Mater. Struct.; vol. 9; 2000; pp. 571-581.
Zhdanov et al.; Thermal stresses in tubes, produced from a melt by the Stepanov method, during their colling; Journal of Engineering Physics and Thermophysics; vol. 68; No. 1; 1995; pp. 80-89.
Johnson, Alfred David; U.S. Appl. No. 12/325,722 entitled "Biocompatible copper-based single-crystal shape memory alloys," filed Dec. 1, 2008.
Johnson, Alfred David; U.S. Appl. No. 12/182,119 entitled "Method and devices for preventing restenosis in cardiovascular stents," filed Jul. 29, 2008.
Johnson et al.; U.S. Appl. No. 12/503,614 entitled "Sprinkler valve with active actuation," filed Jul. 15, 2009.
Dario et al.; Shape memory alloy microactuators for minimal invasive surgery; Proceedings of SMST-94 Conference; pp. 427-433; Pacific Grove CA; 1994.
Johnson, A. D.; Vacuum-deposited TiNi shape memory film: Characterization and applications in microdevices; J. Micromech. Microeng.; vol. 1; pp. 34-41; 1991.
Krulevitch et al.; Thin film shape memory alloy microactuators; J. Micromech. Microeng.; vol. 5; No. 4; 26 pgs.; 1996.
Schetky, L.M.; Shape-memory alloys; Scientific American, pp. 74-82; 1979.

* cited by examiner

TEAR-RESISTANT THIN FILM METHODS OF FABRICATION

CROSS-REFERENCE TO PRIOR APPLICATIONS

This application claims the benefit under 35 USC §119(e) of U.S. provisional patent application Ser. No. 60/666,325 filed Mar. 31, 2005.

BACKGROUND OF THE INVENTION

1. Field of the Invention

The invention relates to thin film materials and devices made therefrom, and more particularly to methods of fabricating thin film with improved tear resistance.

2. Description of the Related Art

Thin film shape memory alloys ("SMA") such as TiNi, also know as Nitinol, are used in many medical applications such as stents and stent covers. For some of these applications bulk material is not suitable due to its stiffness. It is difficult to roll TiNi film to a thickness less than about 30 microns, and the rolling process induces work hardening that makes the material hard and inflexible. Small diameter intravascular devices are made of thin films a few microns in thickness. These devices have the advantage of being extremely flexible, enabling their insertion by catheter into tortuous blood vessels. Foils of 30 microns or less in thickness are most practically made by sputter deposition.

It is generally known that TiNi SMAs lack the property of toughness. In particular, Nitinol is notch sensitive, meaning that a small crack (even microscopic in size) on the surface (and especially at the edge of a sheet) will propagate under stress, and this process is not "self healing" as it is in some other materials. Thin film is particularly vulnerable to crack propagation because it can be easily bent out of plane so that a shear stress becomes a tearing stress.

Improved tear resistance of TiNi thin films will increase their usefulness in many applications, and especially in applications that require long cycle life and in which a failure can be catastrophic. In some medical applications such as heart valve leaflets a tear could be fatal to a patient.

Most tears in thin film materials originate at an edge. A tear in a thin sheet begins with a small crack. Cracks propagate because the crack produces a concentration of stress at the tip of the crack. A well known method of stopping cracks in ductile materials (such as plastics) is to create a hole at the end of the crack. Drilling a hole through a sheet of plastic distributes the tear force over a longer path and thereby eliminates the local stress concentration The need has therefore been recognized for fabrication methods that produce thin film materials having improved tear resistance over available prior art thin film materials. Heretofore there has not been provided a suitable and attractive solution to the problems of tearing in prior art thin film materials.

OBJECTS OF THE INVENTION

A general object of this invention is to provide methods of fabricating thin film materials having improved tear resistance Another object is to provide fabrication methods of the type described which produce thin film materials, such as shape memory alloys, having significantly improved tear resistance in comparison to the prior art thin film materials.

DESCRIPTION OF THE PREFERRED EMBODIMENTS

In its broadest aspect, the present invention fabricates thin film material by forming small holes at every location where a crack can start in the thin film. The word "hole" is defined herein as including openings, perforations or fenestrations. The term "thin film" is defined herein as a film with a thickness of less than 50 microns.

Tear resistance is substantially increased in the invention by fabricating the thin film device with a plurality, such as two, of rows of very small holes along one or more edges of the device and in which the rows are substantially parallel with the edge. The term "small holes" is defined herein as holes having a diameter in the range of approximately 2 to 4 times the thickness of the film. The holes are formed in an overlapping relationship and spaced apart a distance that is sufficiently close so that they will cause any crack, that may propagate substantially perpendicular to an edge of the film, will encounter a hole.

Figure 1:
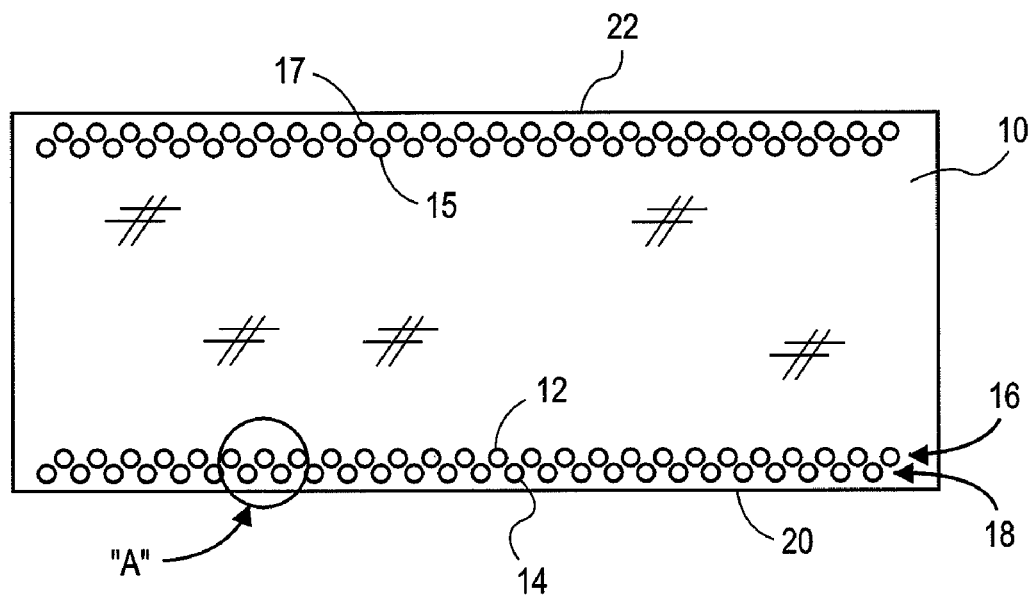
FIG. 1 is a plan view of a rectangular leaf comprising a thin film fabricated with holes formed along edges of the leaf in accordance with one embodiment of the invention.

FIG. 1 shows a rectangular thin film leaf 10 fabricated in accordance with one embodiment of the invention. The thin film is deposited in a thin layer of an SMA material on a suitable substrate (not shown) by through well-known sputter deposition methods. In this example, the film is formed with a thickness of 30 microns. The thickness could be varied in accordance with the requirements of a particular application, within the limit of being less than 50 microns. Using know photo masking and etching methods, a plurality of small holes 12, 14 are fabricated along two or more rows 16, 18 on one side edge 20, and/or holes 15, 17' on other side edges where tear resistance is desired, such as opposite edge 22.

Figure 2:
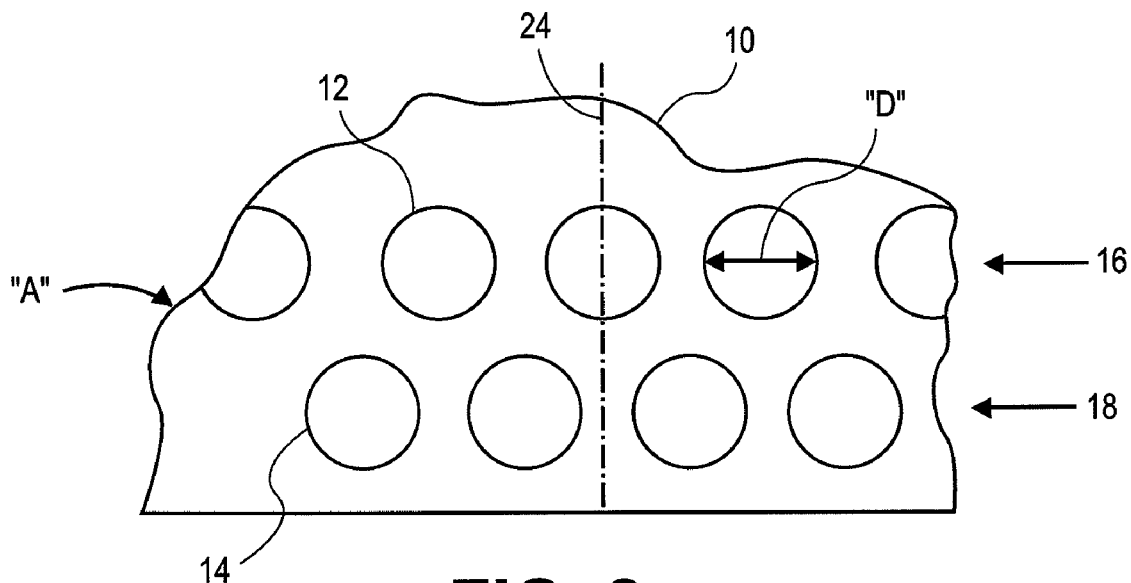
FIG. 2 is a fragmentary, enlarged plan view of the portion of FIG. 1 identified as "A."

The thin film device is fabricated with a particular hole placement in which the holes in one row are in overlapping relationship with the holes an adjacent row. As used herein the term "overlapping relationship" means:

in each row the holes are spaced apart along an axis which extends near to and along an edge of the thin film leaf. As used herein, the term "extends along" means that the axis would substantially conform with the contour of the edge, that is where the edge is straight the axis would be straight and where the edge is in a curve, sawtooth or other form then the axis would be respectively so shaped; and the holes in any one row are offset along that row's axis from the holes in the adjacent row, as shown in FIGS. 1 and 2; and the widths "D" of the holes are sufficiently large so that an imaginary line 24 (FIG. 2), representing a possible tear or crack, extending perpendicular from any location along the edge will intersect at least one hole. In the example of FIGS. 1 and 2 the hole width D can be 60 to 120 microns.

As the tear or crack enters the hole the stress is distributed along the edge of the hole, so the stress concentration is reduced or eliminated.

The size, placement, spacing, and shape of the holes are selected according to the properties of the thin film (e. g. thickness, spacing, size, width, ductility and ultimate strength) to optimize the tear resistance characteristics.

Figure 3:
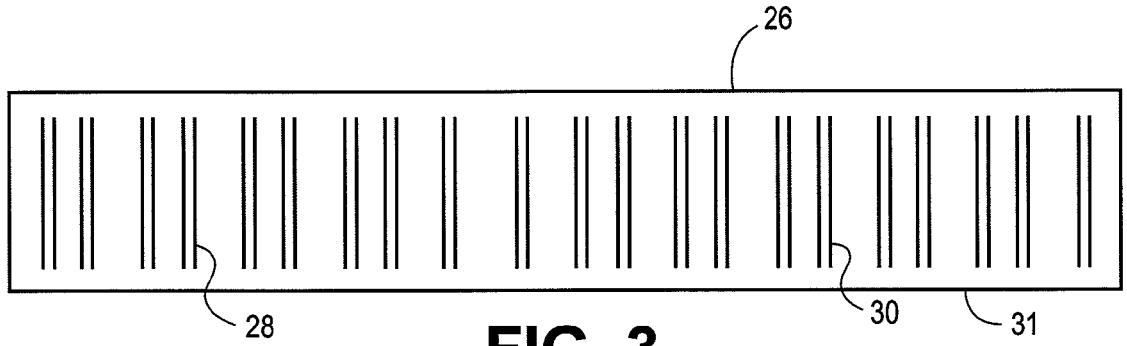
FIG. 3 is a plan view of one component of a thin film fabricated with ribs and struts in accordance with another embodiment the invention.
Figure 4:
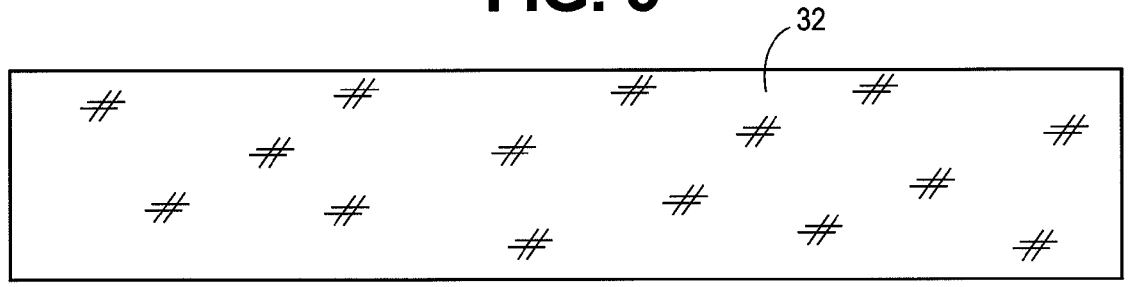
FIG. 4 is a plan view of another component that is used with the embodiment of FIG. 3.
Figure 5:
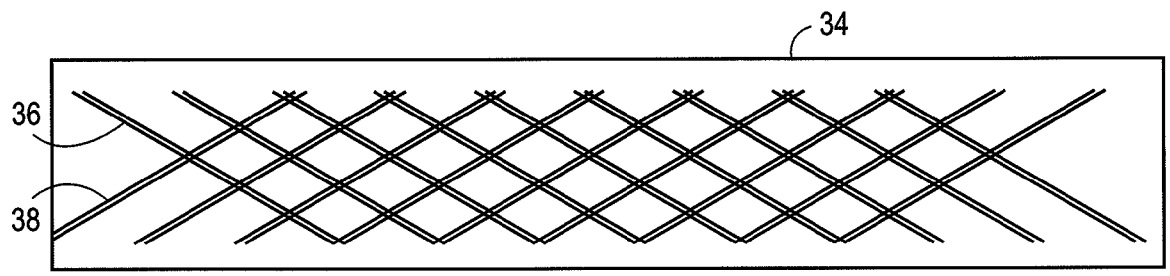
FIG. 5 is a plan view of a further component that is used with the embodiment of FIG. 3.

FIGS. 3-6 show components of an enhanced tear resistant structure that is fabricated by a method in accordance with another embodiment of the invention. In this method thin film tear resistant is achieved by creating a grid of raised ribs or struts that are thicker than the main film. This is done in three layers, using methods employed in the disclosure of U.S. Pat. No. 6,746,890 to Gupta et al. entitled Three Dimensional Thin Film Devices And Methods, which is incorporated by this reference. A first layer 26 shown in FIG. 3 comprising an SMA material is deposited in a plurality of ribs 28, 30 that are laid down in a pattern which is perpendicular to thin film edge 31. Then a second, planar layer 32 of FIG. 4 comprising an SMA material is laid down covering and bonded with the first layer. The third and final layer 34 of SMA material is laid down as shown in FIG. 5 and bonded on top of layer 32 with a grid of ribs 36, 38 oriented at 60 degree angles to the ribs 28, 30 in the first layer. As described herein, in some embodiments, a thin film device having optimum tear resistance includes a thin film first layer 26 of a material (FIG. 3), a thin film second layer 32 (FIG. 4), and a thin film third layer 34 (FIG. 5). The first layer 26 includes a first planar side (as shown in FIG. 3), a second planar side (not shown), and an edge 31. The first side, as shown in FIG. 3, is formed with a plurality of spaced-apart ribs 28, 30 which are inclined at a first angle with respect to the edge 31. The thin film second layer 32 (FIG. 4) includes first and second planar sides, the first side of the second layer being bonded to the second side of the first layer. The thin film third layer 34 (FIG. 5) includes a first planar side (not shown) and a second planar side (as shown in FIG. 5). The first side of the third layer is bonded to the second side of the second layer, and the second side of the third layer, as shown in FIG. 5, is formed with a plurality of spaced-apart struts 36, 38 which are inclined a second angle with respect to the edge.

Figure 6:
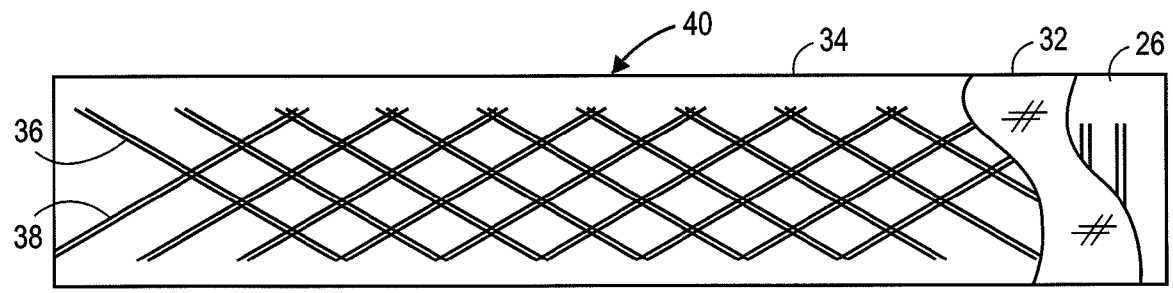
FIG. 6 is a plan view of a thin film device comprising the components of FIGS. 3-5.

FIG. 6 shows the final thin film device 40 comprising the three layers 26, 32 and 34 bonded together and forming a single piece of metal having ribbed patterns on opposite sides of the plain layer 32. This patterning resists tearing because the grid struts are at an angle to the tear so that part of each is in linear tension, which is stronger than the material that is in tearing tension. In addition, the middle layer can be made of a higher-transition-temperature SMA material than the ribs. This material is in martensite crystal structure, which means that it may deform several percent without fracturing. It is desirable that this middle layer material is very ductile; or at least more ductile than the ribbed layers. The ductile layer spreads the stress out over a much larger dimension than the end of the crack, so the crack does not readily propagate.

An alternative configuration (not shown) that is simpler to fabricate, comprises a plane layer of ductile material as the first layer and a second layer having vertical struts and struts at 30 degrees and 150 degrees to the positive thins film edge. The hole patterns can be oblong instead of circular to distribute stress. Borders of the holes may be of a ductile material. The holes of the embodiment of FIGS. 1 and 2 and struts of the embodiment of FIGS. 3-6 may also be combined.

In a configuration comprising struts, the field between the struts should be of a ductile material. The film properties (strength, modulus of elasticity, thickness and transition temperature) must be selected so that the force of tear is optimally distributed by being transferred to a strut in tension. The operating principle of the strut design is that the shear stress is transferred to longitudinal stress of the strut and its strength is much greater in tension than in shear.

The crack propagation rate is to the tenth power of the tensile stress. Thus, reduction of tensile stress by even a very little bit magnifies the tearing characteristics.

The invention claimed is:

1. A thin film device having optimum tear resistance, the device comprising a thin film first layer of a material, the first layer having first and second planar sides, the layer having an edge, the first side being formed with a plurality of spaced-apart ribs which are inclined at a first angle with respect to the edge, a thin film second layer having first and second planar sides, the first side of the second layer being bonded to the second side of the first layer, a thin film third layer having first and second planar sides, the first side of the third layer being bonded to the second side of the second layer, and the second side of the third layer being formed with a plurality of spaced-apart struts which are inclined a second angle with respect to the edge.

2. A thin film device as in claim 1 in which the material is a shape memory alloy.

3. A method of fabricating a thin film device with improved tear resistance comprising the steps of providing a thin film first layer of a material having first and second planar sides and with the layer having an edge, forming the first side being with a plurality of spaced-apart ribs which are inclined at a first angle with respect to the edge, forming a thin film second layer having first and second planar sides, bonding the first side of the second layer to the second side of the first layer, forming a thin film third layer having first and second planar sides, bonding the first side of the third layer to the second side of the second layer, and forming the second side of the third layer with a plurality of spaced-apart struts which are inclined a second angle with respect to the edge.

4. A method as in claim 3 in which a shape memory alloy is provided as the material.

5. A tear-resistant thin film device, the device formed by the combination of three layers, the device comprising:
   a first thin film layer of a shape memory alloy material, the first layer comprising an inner planar surface opposite an outer surface, the outer surface having a plurality raised ribs extending therealong;
   a second thin film layer of shape memory alloy material bonded to the inner planar surface; and
   a third thin film layer of shape memory alloy, the third layer comprising an inner planar surface and an outer planar surface, wherein the inner planar surface of the third layer is bonded to the second thin film layer and the outer surface of the third layer comprises a plurality of raised struts which are inclined at an angle with respect to the ribs.

6. The tear-resistant thin-film device of claim 5, wherein the first and third layers are each thicker than the second layer.

7. The tear-resistant thin-film device of claim 5, wherein the second layer comprises a shape memory alloy having a higher transition temperature than the shape memory alloy forming either the first or third layers.

8. The tear-resistant thin-film device of claim 5, wherein the second layer is formed of a shape memory alloy that is more ductile than the shape memory alloy materials forming the first and third layers.

9. The tear-resistant thin-film device of claim 5, wherein the angle between the raised struts and the ribs is about 60 degrees.

10. A tear-resistant thin film device comprising:
- a thin film layer comprising a plane of a shape memory alloy material, the thin film layer having a first planar side and a second planar side;
- a plurality of raised ribs bonded to the first planar side of the thin film layer, wherein the ribs are formed of a shape memory alloy material; and
- a plurality of raised struts bonded to the second planar side of the thin film layer which are inclined at an angle with respect to the ribs, wherein the struts are formed of a shape memory alloy material;
- wherein the shape memory material forming the thin film layer is different from the shape memory alloy material forming the ribs and the shape memory alloy material forming the struts.

11. The tear-resistant thin-film device of claim 10, wherein the ribs and the struts are each thicker than the thin film layer.

12. The tear-resistant thin-film device of claim 10, wherein the shape memory alloy material forming the thin film layer has a higher transition temperature than the shape memory alloy material forming the ribs and the shape memory alloy material forming the struts.

13. The tear-resistant thin-film device of claim 10, wherein the ribs and the struts are formed of the shame shape memory alloy material.

14. The tear-resistant thin-film device of claim 10, wherein the shape memory alloy material forming the thin film layer is more ductile than the shape memory alloy material forming the ribs and the shape memory alloy material forming the struts.

15. The tear-resistant thin-film device of claim 10, wherein the angle between the ribs and the struts is about 60 degrees.

* * * * *